US009394346B2

(12) United States Patent
Livshits et al.

(10) Patent No.: US 9,394,346 B2
(45) Date of Patent: *Jul. 19, 2016

(54) METHOD FOR PRODUCING AN AMINO ACID USING A BACTERIUM OVEREXPRESSING AN RHTC GENE

(75) Inventors: Vitaliy Arkadyevich Livshits, Moscow (RU); Natalia Pavlovna Zakataeva, Moscow (RU); Vladimir Veniaminovich Aleshin, Moscow (RU); Alla Valentinovna Belareva, Moscow (RU); Irina Lyvovna Tokhmakova, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 2066 days.

This patent is subject to a terminal disclaimer.

(21) Appl. No.: 11/106,455

(22) Filed: Apr. 15, 2005

(65) Prior Publication Data

US 2005/0239177 A1    Oct. 27, 2005

Related U.S. Application Data

(62) Division of application No. 09/466,935, filed on Dec. 20, 1999, now abandoned.

(30) Foreign Application Priority Data

Dec. 23, 1998  (RU) .................................. 98123511

(51) Int. Cl.
| *C12P 13/06* | (2006.01) |
| *C12P 13/08* | (2006.01) |
| *C07K 14/245* | (2006.01) |

(52) U.S. Cl.
CPC .............. *C07K 14/245* (2013.01); *C12P 13/06* (2013.01); *C12P 13/08* (2013.01)

(58) Field of Classification Search
None
See application file for complete search history.

(56) References Cited

U.S. PATENT DOCUMENTS

| 3,830,696 A | 8/1974 | Daum et al. |
| 4,321,325 A * | 3/1982 | Debabov et al. ............... 435/115 |
| 5,175,107 A | 12/1992 | Debabov et al. |
| 5,508,192 A * | 4/1996 | Georgiou et al. .......... 435/252.3 |
| 5,538,873 A | 7/1996 | Debabov et al. |
| 5,589,364 A | 12/1996 | Williams et al. |
| 5,631,157 A | 5/1997 | Debabov et al. |
| 5,658,766 A | 8/1997 | Livshits et al. |
| 5,705,371 A | 1/1998 | Debabov et al. |
| 5,976,843 A | 11/1999 | Debabov et al. |
| 6,132,999 A | 10/2000 | Debabov et al. |
| 6,165,756 A | 12/2000 | Debabov et al. |
| 6,303,348 B1 | 10/2001 | Livshits et al. |
| 6,858,406 B1 | 2/2005 | Vrljic et al. |
| 2002/0058314 A1 | 5/2002 | Livshits et al. |

FOREIGN PATENT DOCUMENTS

| DE | 195 48 222 | 6/1997 |
| WO | WO 97/23597 | 7/1997 |

OTHER PUBLICATIONS

"Current Protocols in Molecular Biology," Ausubel et al., John Wiley and Sons, Inc., New York, 1993, Unit 2.9A pp. 1-2 and Unit 2.10, pp. 1-16.*
Freundlich et al., PNAS 48:1804-1808, 1962.*
Witkowski et al., Biochemistry 38:11643-11650, 1999.*
Brenner, Trends Genet 15:132-133, 1999.*
Lee et al., "Systems metabolic engineering of *Escherichia coli* for L-threonine production", Mol. Systems Biol. 3, article 149, pp. 1-8, 2007.*
Jetten et al., "Recent Advances in the Physiology and Genetics of Amino Acid-Producing Bacteria", Crit. Rev. Biotechnol. 15:73-103, 1995.*
Daniels et al., "Analysis of the *Escherichia coli* Genome: DNA Sequence of the Region from 84.5 to 86.5 Minutes", Science 257:771-778, 1992.*
Singh et al., The Plant Cell 7:935-944, 1995.*
KEGG database entry for ECs4753, obtained from http://www.genome.jp/dbget-bin/www_bget?ecs:ECs4753, last viewed on Mar. 3, 2011, 1 page.*
Revision history for GenBank Accession No. 15834007, obtained from www.ncbi.nlm.nih.gov/sviewer/girevhist.cgi?val=NP_312780.1&log$=seqview, last viewed on Mar. 3, 2011, 2 pages.*
Aleshin, V. V., et al., "A New Family of Amino-Acid-Efflux Proteins," TIBS 1999;24(4):133-135.
Astaurova, O. R., et al., "Amination in Strains of *Escherichia coli* Which Effectively Synthesize Threonine," App. Biochem. Microbiol. 1986;21(5):485-490.
Astaurova, O. B., et al., "Comparative Study of Amino-Acid-Producing *E. coli* Strains," App. Biochem. Microbiol. 1992;27(5):556-561.
Branden, et al., "Introduction to Protein Structure," Garland Publishing Inc., New York, 1991.
Daniels, D. L., et al., "*E. coli* Genomic Sequence of the Region from 84.5 to 86.5 Minutes," Aug. 1, 1992 (Abstract only, 5 pp.) XP-002135074.
Lomovskaya, O. L., et al., "Characterization of the $\sigma^{38}$-Dependent Expression of a Core *Escherichia coli* Starvation Gene, *pexB*," App. Biochem. Microbiol. 1994;176(13):3928-3935.

(Continued)

*Primary Examiner* — David J Steadman
(74) *Attorney, Agent, or Firm* — Shelly Guest Cermak; Cermak Nakajima & McGowan LLP

(57) ABSTRACT

The present invention describes a bacterium which has an ability to produce an amino acid and in which the rhtC gene encoding a protein having an enhanced activity of imparting L-threonine resistance to a bacterium expressing the protein. Preferably, the bacterium further includes an rhtB gene encoding for a protein having an enhanced activity of imparting to a bacterium L-homoserine resistance expressing the protein. The present invention also describes a method of cultivating the bacterium in a culture medium to produce and accumulate amino acids in the medium, and the amino acid is recovered from the medium.

6 Claims, 4 Drawing Sheets

(56) References Cited

OTHER PUBLICATIONS

Palmieri, L., et al., "Threonine Diffusion and Threonine Transport in Corynebacterium Glutamicum and Their Role in Threonine Production," Arch. Microbiol. 1996;165(1):48-54.

Zakataeva, N. P., et al., "Characterization of a Pleiotropic Mutation That Confers Upon *Escherichia coli* Cells Resistance to High Concentrations of Hooserine and Threonine," Abstracts of the 17$^{th}$ International Congress of Biochemistry and Molecular Biology in conjunction with the 1997 Annual Meeting of the American Society for Biochemistry and Molecular Biology, Abstract No. 457, 1 page, Aug. 24-29, 1997.

Zakataeva, N. P., et al., "The Novel Transmembrane *Escherichia coli* Proteins Involved in the Amino Acid Efflux," FEBS Letters 1999;452;228-232.

Kruse, D., et al., "Influence of threonine exporters on threonine production in *Escherichia coli*," Appl. Microbiol. Biotechnol. 2002;59:205-210.

Kobayashi, T., et al., "Gene Organization of *pldA* and *pldB*, the Structural Genes for Detergent-Resistant Phospholipase A and Lysophospholipase L$_2$ of *Escherichia coli*," J. Biochem. 1985;98:1007-1016.

Homma, H., et al., "Identification and Cloning of the Gene Coding for Lysophospholipase L$_2$ of *E. coli* K-12$^1$" J. Biochem 1983;94:2079-2081.

Pending U.S. Appl. No. 09/137,695, filed Aug. 21, 1998.
Pending U.S. Appl. No. 09/459,573, filed Dec. 13, 1999.
Pending U.S. Appl. No. 09/466,935, filed Dec. 20, 1999.

Begot, C., et al., "Recommendations of calculating growth parameters by optical density measurements," J. Microbiol. Methods 1996;25:225-232.

Hanko, V. P., et al., "Determination of amino acids in cell culture and fermentation broth media using anion-exchange chromatography with integrated pulsed amperometric detection," Analytical Biochem. 2004;324;29-38.

Kaplan, M. M., et al., "Threonine Biosynthesis on the Pathway in Fungi and Bacteria and the Mechanism of the Isomerization Reaction," J. Bio. Chem. 1965;240:3928-3933.

Daniels, D. L., et al, NCBI Database Acc. No. P27846 version of Jul. 15, 1998: "Hypothetical 22.5 KD Protein in recQ-pldB intergenic region," pp. 1-2.

Makrides, S.C., "Strategies for Achieving High-Level Expression of Genes in *Escherichia coli*," Microbiol. Rev. 1996;60(3):512-538.

Vrljic, M., et al., "A new type of transporter with a new type of cellular function: L-lysine export from *Corynebacterium glutamicum*," Mol. Microbiol. 1996;22(5):815-826.

Zakataeva, N. P., et al., "Characterization of a pleiotropie mutation that confers upon *Escherichia coli* cells resistance to high concentrations of homoserine and threonine," FASEB Journal 1997;1 1(9):p. a935.

Römpp, Lexikon Biochemie and Molekularbiologie, 2000, p. 266.
Biochemistry, Berg et al., 5$^{th}$ Ed. 2002, pp. 174-179.
Alignment/Sequence Listing of rhtC and c-rhtC, as explained in Opponent's Letter (p. 2), May 14, 2010.
Opponent'S Letter to the EPO for European Patent App. 99125406.1 (May 14, 2010) with English translation.

* cited by examiner

US 9,394,346 B2

METHOD FOR PRODUCING AN AMINO ACID USING A BACTERIUM OVEREXPRESSING AN RHTC GENE

This application claims the benefit of U.S. patent application Ser. No. 09/466,935 filed Dec. 20, 1999, now abandoned as a divisional under 35 U.S.C. §120.

BACKGROUND OF THE INVENTION

1. Field of the Invention

The present invention relates to biotechnology, and more specifically to a method for producing amino acids. The present invention more specifically relates to a method for producing L-homoserine, L-threonine, L-valine, or L-leucine using a bacterium belonging to the genus Escherichia.

2. Brief Description of the Related Art

The present inventors obtained, with respect to E. coli K-12, a mutant having a mutation, thrR (herein referred to as rhtA23) that confers resistance to high concentrations of threonine or homoserine in a minimal medium (Astaurova, O. B. et al., Appl. Bioch. And Microbiol., 21, 611-616 (1985)). The mutation resulted in improved production of L-threonine (SU Patent No. 974817), homoserine, and glutamate (Astaurova, O. B. et al., Appl. Bioch. And Microbiol., 27, 556-561, 1991) by the respective E. coli producing strains.

Furthermore, the present inventors have revealed that the rhtA gene exists at 18 min on E. coli chromosome, and that the rhtA gene is identical to the ORF1 between the pexB and ompX genes. The unit expressing a protein encoded by the ORF has been designated the rhtA (rht: resistance to homoserine and threonine) gene. The rhtA gene includes a 5'-noncoding region which includes a SD sequence, ORF1, and a terminator. Also, the present inventors have found that a wild-type rhtA gene imparts resistance to threonine and homoserine if cloned in a multicopy state, and that the rhtA23 mutation is an A-for-G substitution at position −1 with respect to the ATG start codon (ABSTRACTS of 17$^{th}$ International Congress of Biochemistry and Molecular Biology in conjugation with 1997 Annual Meeting of the American Society for Biochemistry and Molecular Biology, San Francisco, Calif. Aug. 24-29, 1997, abstract No. 457).

During cloning of the rhtA gene, at least two different genes were found which impart threonine and homoserine resistance when in a multicopy state in E. coli. One is the rhtA gene, and the other gene was found to be the rhtB gene, which confers homoserine resistance (Russian Patent Application No. 98118425).

SUMMARY OF THE INVENTION

An object of the present invention is to provide a method for producing an amino acid, especially L-homoserine, L-threonine, and branched chain amino acids with a higher yield.

The inventors have found that a region at 86 min on the E. coli chromosome, when cloned into a multicopy vector, is able to impart resistance to L-homoserine to cells of E. coli. The inventors further found that there exists in the upstream region another gene, rhtC, which involves resistance to threonine, and that when these genes are amplified, the amino acid productivity of E. coli can be improved similar to the rhtA gene. On the basis of these findings, the present invention has been completed.

It is an object of the present invention to provide a bacterium belonging to the genus Escherichia, wherein L-threonine resistance of the bacterium is enhanced by enhancing an activity of a protein selected from the group consisting of:

(A) a protein comprising the amino acid sequence of SEQ ID NO: 4; and (B) a protein comprising the amino acid sequence of SEQ ID NO: 4 which includes deletion, substitution, insertion or addition of one or several amino acids, and which has an activity of imparting resistance to L-threonine to a bacterium expressing the protein.

It is a further object of the present invention to provide the bacterium as described above, wherein L-homoserine resistance of the bacterium is further enhanced by enhancing an activity of protein selected from the group consisting of:

(C) a protein comprising the amino acid sequence of SEQ ID NO: 2; and (D) a protein comprising the amino acid sequence of SEQ ID NO: 2 which includes deletion, substitution, insertion or addition of one or several amino acids, and which has an activity of imparting resistance to L-homoserine to a bacterium expressing the protein.

It is a further object of the present invention to provide the bacterium as described above, wherein said activity is enhanced by transformation of the bacterium with DNA coding for the protein as defined above.

It is a further object of the present invention to provide a method for producing an amino acid comprising cultivating said bacterium as defined above in a culture medium, and recovering said amino acid from the medium.

It is a further object of the present invention to provide the method as described above, wherein said amino acid is selected from the group consisting of L-homoserine, L-threonine, and branched chain amino acids.

It is a further object of the present invention to provide the method as described above wherein said branched chain amino acid comprises L-valine or L-leucine.

It is a further object of the present invention to provide a DNA encoding a protein selected from the group consisting of:

(A) a protein comprising the amino acid sequence of SEQ ID NO: 4;

(B) a protein comprising the amino acid sequence of SEQ ID NO: 4 which includes substitution, deletion, insertion, addition, or inversion of one or several amino acids, and has an activity of imparting L-threonine resistance to a bacterium expressing the protein.

It is a further object of the present invention to provide the DNA as described above which is selected from the group consisting of:

(a) a DNA comprising the nucleotide sequence of numbers 187 to 804 in SEQ ID NO: 3; and (b) a DNA which is able to hybridize with a nucleotide sequence of numbers 187 to 804 in SEQ ID NO: 3 or a probe prepared from the nucleotide sequence under stringent conditions, and encodes a protein having an activity of imparting L-threonine resistance to a bacterium expressing the protein.

It is a further object of the present invention to provide the DNA as described above wherein the stringent conditions comprise washing at 60° C., and at a salt concentration corresponding to 1×SSC and 0.1% SDS.

DETAILED DESCRIPTION OF THE PREFERRED EMBODIMENTS

Figure 1:
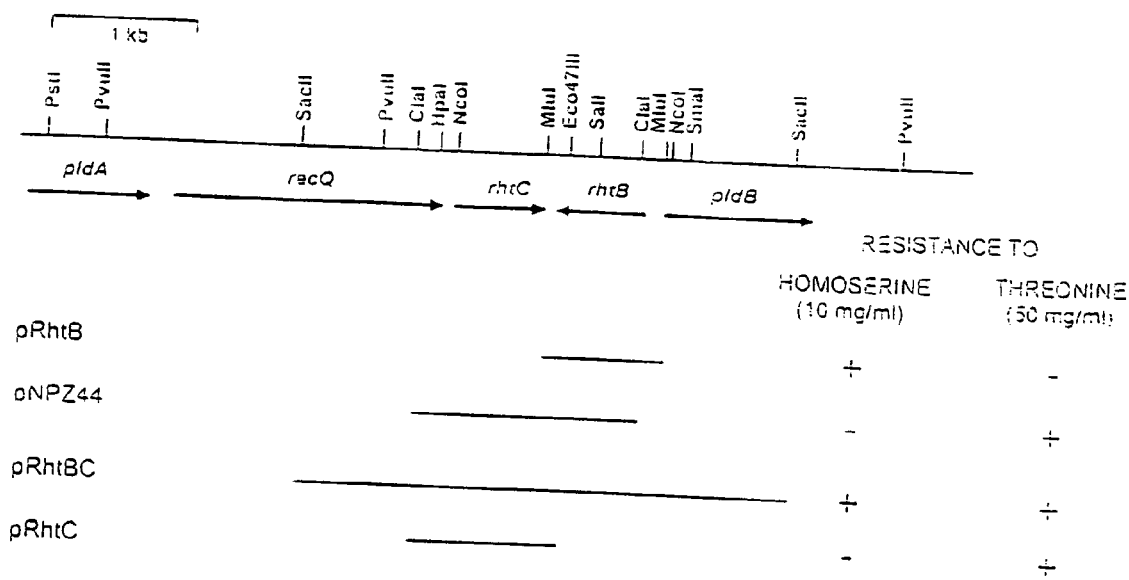
FIG. 1 shows the cloning and identification of rhtB and rhtC genes.

The DNA fragment coding for the protein as defined in (A) or (B) above may be referred to as the "rhtC gene," a protein encoded by the rhtC gene may be referred to as the "RhtC protein," the DNA coding for the protein as defined as (C) or (D) above may be referred to as the "rhtB gene," a protein coded by the rhtB gene may be referred to as the "RhtB protein." An activity of the RhtC protein of causing resistance to L-threonine in a bacterium (i.e. an activity of marking a bacterium having the RhtC protein L-threonine-resistant) may be referred to as "Rt activity," and an activity of the RhtB protein of causing resistance to L-homoserine in a bacterium (i.e. an activity of marking a bacterium having the RhtB protein L-homoserine-resistant) may be referred to as "Rh activity." A structural gene encoding the RhtC protein or RhtB protein may be referred to as the "rhtC structural gene" or "rhtB structural gene." The phrase "enhancing the Rt activity or the Rh activity" means imparting resistance to threonine or homoserine to a bacterium or enhancing the resistance by increasing the number of molecules of the RhtC protein or RhtB protein. This is accomplished by increasing the specific activity of these proteins, or desensitizing negative regulation of the expression or activity of these proteins, or the like. The phrase "DNA coding for a protein" means a DNA whereby one of strands codes for the protein when the DNA is double-stranded. The L-threonine resistance means that a bacterium is able to grow on a minimal medium containing L-threonine at a concentration at which a wild-type strain thereof would not grow, usually at >30 mg/ml. The L-homoserine resistance means that a bacterium grows on a minimal medium containing L-homoserine at a concentration at which a wild-type strain thereof would not grow, usually at >5 mg/ml. The ability to produce an amino acid means that a bacterium is able to produce and cause accumulation of the amino acid in a medium in a larger amount than a wild-type strain thereof.

According to the present invention, resistance to threonine, or to threonine and homoserine at a high concentration, can be imparted to a bacterium belonging to the genus *Escherichia*. A bacterium belonging to the genus *Escherichia* has increasing resistance to threonine, or to threonine and homoserine, and an ability to accumulate an amino acid, especially L-homoserine, L-threonine, or branched chain amino acids such as L-valine and L-leucine, in a medium with a high yield.

The present invention will be explained in detail below.

<1> DNA Used for the Present Invention

One of the DNA fragments of the present invention, the rhtC gene, codes for a protein having Rt activity and having the amino acid sequence of SEQ ID NO: 4. Specifically, the DNA may be exemplified by a DNA comprising a nucleotide sequence of the numbers 187 to 804 of SEQ ID NO: 3.

Another DNA fragment of the present invention, the rhtB gene, codes for a protein having Rh activity and the amino acid sequence of SEQ ID NO: 2. Specifically, the DNA may be exemplified by a DNA comprising a nucleotide sequence of the numbers 557 to 1171 of SEQ ID NO: 1.

The rhtB gene having the nucleotide sequence of SEQ ID NO: 1 corresponds to a part of a sequence complementary to the sequence of GenBank accession number M87049, and includes f138 (nucleotide numbers 61959-61543 of M87049) which is an ORF (open reading frame) present at 86 min on *E. coli* chromosome of unknown function, and the 5'- and 3'-flanking regions thereof. The f138, which had only 160 nucleotides in the 5'-flanking region, was not able to impart resistance to homoserine. No termination codon is present between the 62160 and 61959 nucleotides of M87049 (upstream to the ORF f138). Moreover, one of the ATG codons of this sequence is preceded by a ribosome-binding site (62171-62166 in M87049). Hence, the coding region is 201 bp longer. The larger ORF (nucleotide numbers 62160 to 61546 of M87049) is designated the rhtB gene.

The rhtB gene may be obtained, for example, by infecting an *E. coli* Mucts lysogenic strain using a lysate of a strain of *E. coli* such as K12 or W3110 using a mini-Mu d5005 phagemid method (Groisman, E. A., et al., J. Bacteriol., 168, 357-364 (1986)), and isolating phagemid DNAs from colonies which grow on a minimal medium containing kanamycin (40 µg/ml) and L-homoserine (10 mg/ml). As illustrated in the Example described below, the rhtB gene was mapped at 86 min on the chromosome of *E. coli*. Therefore, the DNA fragment containing the rhtB gene may be obtained from the chromosome of *E. coli* by colony hybridization or PCR (polymerase chain reaction, refer to White, T. J. et al, Trends Genet. 5, 185 (1989)) using oligonucleotide(s) which corresponding to a region near the portion at 86 min on the chromosome *E. coli*.

Alternatively, an oligonucleotide may be designed based on the nucleotide sequence of SEQ ID NO: 1. The entire coding region can be amplified by PCR using oligonucleotides as primers which have nucleotide sequences corresponding to an upstream region from the number 557 and a downstream region from the nucleotide number 1171 in SEQ ID NO: 1.

Synthesis of the oligonucleotides can be performed by an ordinary method such as a phosphoamidite method (see *Tetrahedron Letters,* 22, 1859 (1981)) by using a commercially available DNA synthesizer (for example, DNA Synthesizer Model 380B produced by Applied Biosystems). Furthermore, the PCR can be performed by using a commercially available PCR apparatus (for example, DNA Thermal Cycler Model PJ2000 produced by Takara Shuzo Co., Ltd.) using Taq DNA polymerase (supplied by Takara Shuzo Co., Ltd.) in accordance with a method designated by the supplier.

The rhtC gene was obtained from the DNA fragment which contains the rhtB gene during the cloning of rhtB as described later in the examples. The rhtC gene corresponds to a corrected, as described below, sequence of O128 (nucleotide numbers 60860-61480 of GeneBank accession number M87049) which is a known ORF, but the function is unknown. The rhtC gene may be obtained by PCR or hybridization using oligonucleotides based on the nucleotide sequence of SEQ ID NO: 3. By using oligonucleotides having nucleotide sequence corresponding to a upstream region from nucleotide number 187 and a downstream region from the nucleotide number 804 in SEQ ID NO: 3 as the primers for PCR, the entire coding region can be amplified.

In the present invention, the DNA coding for the RhtB protein of the present invention may code for the RhtB protein which includes deletion, substitution, insertion, or addition of one or several amino acids at one or a plurality of positions, provided that the Rh activity of the RhtB protein encoded thereby is maintained. Similarly, the DNA coding for the RhtC protein of the present invention may code for RhtC protein which includes deletion, substitution, insertion, or addition of one or several amino acids at one or a plurality of positions, provided that the Rt activity of the RhtC protein encoded thereby is maintained.

The DNA which codes for substantially the same protein as the RhtB or RhtC protein as described above, may be obtained, for example, by modifying the nucleotide sequence, for example, by means of the site-directed mutagenesis method so that one or more amino acid residues at a specified site have a deletion, substitution, insertion, or addition. DNA modified as described above may be obtained by conventionally known mutation treatments. Such treatments include a method for treating a DNA coding for the RhtB protein or RhtC protein in vitro, for example, with hydroxylamine, and a method for treating a microorganism, for example, a bacterium, belonging to the genus *Escherichia* harboring a DNA coding for the RhtB protein with ultraviolet irradiation or a mutating agent such as N-methyl-N'-nitro-N-nitrosoguanidine (NTG) and nitrous acid typically used for such mutation treatments.

The DNA which codes for substantially the same protein as the RhtB or RhtC protein can by obtained by expressing a DNA subjected to an in vitro mutation treatment as described above in multiple copies in an appropriate cell, investigating the resistance to homoserine or threonine, and selecting DNAs which increase the resistance.

It is generally known that an amino acid sequence of a protein and a nucleotide sequence coding for it may be slightly different between species, strains, mutants or variants.

Therefore, the DNA which codes for substantially the same protein as the RhtC protein, can be obtained by isolating a DNA which hybridizes with DNA having, for example, a nucleotide sequence of the numbers 187 to 804 of SEQ ID NO: 3, or a probe obtainable therefrom under stringent conditions, and which codes for a protein having Rt activity from a bacterium belonging to the genus *Escherichia* which is subjected to mutation treatment, or a spontaneous mutant or a variant of a bacterium belonging to the genus *Escherichia*.

Also, the DNA, which codes for substantially the same protein as the RhtB protein, can be obtained by isolating a DNA which hybridizes with DNA having, for example, a nucleotide sequence of the nucleotide numbers 557 to 1171 of the nucleotide sequence of SEQ ID NO: 1 or a probe obtainable therefrom under stringent conditions, and which codes for a protein having the Rh activity, from a bacterium belonging to the genus *Escherichia* which is subjected to mutation treatment, or a spontaneous mutant or a variant of a bacterium belonging to the genus *Escherichia*.

The term "stringent conditions" referred to herein is a condition under which a so-called specific hybrid is formed, and a non-specific hybrid is not formed. It is difficult to clearly express this using a numerical value. However, for example, stringent conditions include a condition under which DNAs having high homology, for example, DNAs having homology of not less than 70% to each other are able to hybridize, and DNAs having homology to each other lower than the above are not able to hybridize. Alternatively, stringent conditions are exemplified by a condition under which DNA's are hybridized to each other at a salt concentration corresponding to an ordinary condition of washing in Southern hybridization, i.e., 60° C., 1×SSC, 0.1% SDS, preferably 0.1×SSC, 0.1% SDS.

<2> Bacterium Belonging to the Genus *Escherichia* of the Present Invention

The bacterium belonging the genus *Escherichia* of the present invention may belong to the genus *Escherichia* and have enhanced Rt activity. A preferred embodiment of the bacterium of the present invention is a bacterium which has further enhanced Rh activity. A bacterium belonging to the genus *Escherichia* is exemplified by *Escherichia coli*. The Rt activity can be enhanced by, for example, amplification of the copy number of the rhtC structural gene in a cell, or transformation of a bacterium belonging to the genus *Escherichia* with a recombinant DNA including the rhtC structural gene ligated to a promoter sequence which functions efficiently in a bacterium belonging to the genus *Escherichia*. The Rt activity can be also enhanced by substitution of the promoter sequence of the rhtC gene on a chromosome with a promoter sequence which functions efficiently in a bacterium belonging to the genus *Escherichia*.

Furthermore, the Rh activity can be enhanced by, for example, amplification of the copy number of the rhtB structural gene in a cell, or transformation of a bacterium belonging to the genus *Escherichia* with recombinant DNA including the rhtB structural gene ligated to a promoter sequence which functions efficiently in a bacterium belonging to the genus *Escherichia*. The Rh activity can be also enhanced by substitution of the promoter sequence of the rhtB gene on a chromosome with a promoter sequence which functions efficiently in a bacterium belonging to the genus *Escherichia*.

The amplification of the copy number of the rhtC structural gene or rhtB structural gene in a cell can be performed by introduction of a multicopy vector which carries the rhtC structural gene or rhtB structural gene into a bacterial cell belonging to the genus *Escherichia*. Specifically, the copy number can be increased by introduction of a plasmid, a phage, or a transposon (Berg, D. E. and Berg, C. M., Bio/Technol., 1, 417 (1983)) which carries the rhtC or rhtB structural gene into a cell of a bacterium belonging to the genus *Escherichia*.

The multicopy vector is exemplified by plasmid vectors such as pBR322, pMW118, pUC19, or the like, and phage vectors such as λ1059, λBF101, M13 mp9, or the like. The transposon is exemplified by Mu, Tn10, Tn5, or the like.

The introduction of a DNA into a bacterium belonging to the genus *Escherichia* can be performed, for example, by a method of D. M. Morrison (Methods in Enzymology, 68, 326 (1979)), or a method in which a recipient bacterial cell is treated with calcium chloride to increase the permeability of DNA (Mandel, M. And Higa, A., J. Mol. Biol., 53, 159, (1970)) and the like.

If the Rt activity, or both the Rt activity and the Rh activity is enhanced in an amino acid-producing bacterium belonging to the genus *Escherichia* as described above, the amount of the amino acid produced can be increased. As the bacterium belonging to the genus *Escherichia* of the present invention, strains which have an inherent ability to produce desired amino acids can be used. Furthermore, the ability to produce an amino acid may be imparted to a bacterium of the present invention.

On the basis of the rhtC DNA fragment amplification, the new strains *E. coli* MG442/pRhtC which is able to produce homoserine; *E. coli* MG442/pVIC40, pRhtC which is able to produce threonine; *E. coli* NZ10/pRhtBC and *E. coli* NZ10/pRhtB, pRhtC which are able to produce homoserine, valine, and leucine, were obtained. These strains are able to cause accumulation of these amino acids in a higher amount than those containing no amplified rhtC DNA fragment.

The new strains have been deposited (according to the Budapest Treaty) in the All-Russian Collection for Industrial Microorganisms (VKPM). The strain *E. coli* MG442/pRhtC was granted accession number VKPM B-7700; the strain *E. coli* MG442/pVIC40, pRhtC was granted accession number VKPM B-7680; the strain *E. coli* NZ10/pRhtB, pRhtC was granted accession number VKPM B-7681, and the strain *E. coli* NZ10/pRhtBC was granted accession number VKPM B-7682.

The strain *E. coli* MG442/pRhtC (VKPM B-7700) exhibits the following culture, morphological, and biochemical features.

Cytomorphology:

Gram-negative weakly-motile rods having rounded ends. Longitudinal size: 1.5 to 2 µm.

Culture Features: Beef-Extract Agar:

After 24 hours of growth at 37° C., round whitish semitransparent colonies 1.0 to 3 mm in diameter are produced, featuring a smooth surface, regular or slightly wavy edges, a slightly raised center, a homogeneous structure, a pastelike consistency, and are readily emulsifiable.

Luria's Agar:

After a 24-hour growth at 37° C., whitish semitranslucent colonies 1.5 to 2.5 mm in diameter develop which have a smooth surface, homogeneous structure, pastelike consistency, and are readily emulsifiable.

Minimal Agar-Doped Medium M9:

After 40 to 48 hours of growth at 37° C., colonies 0.5 to 1.5 mm in diameter form, which are colored grayish-white, semitransparent, slightly convex, and with a lustrous surface.

Growth in a Beef-Extract Broth:

After a 24-hour growth at 37° C., strong uniform cloudiness, having a characteristic odor is observed.

Physiological and Biochemical Features—

Grows upon thrust inoculation in a beef-extract agar: Exhibits good growth throughout the inoculated area. The microorganism proves to be a facultative anaerobe.

It does not liquefy gelatin.

Features a good growth on milk, accompanied by milk coagulation.

Does not produce indole.

Temperature conditions: Grows on beef-extract broth at 20-42° C., an optimum temperature of within 33-37° C.

pH value of culture medium: Grows on liquid media having a pH from 6 to 8, an optimum value being 7.2.

Carbon sources: Exhibits good growth on glucose, fructose, lactose, mannose, galactose, xylose, glycerol, mannitol to produce an acid and gas.

Nitrogen sources: Assimilates nitrogen in the form of ammonium, nitric acid salts, as well as from some organic compounds.

Resistant to ampicillin. L-isoleucine is used as a growth factor. However, the strain can grow slowly without isoleucine.

Content of plasmids: The cells contain the multicopy hybrid plasmid pRhtC which ensures resistance to ampicillin (100 mg/l) and carries the rhtC gene responsible for the increased resistance to threonine (50 mg/ml). The strain *E. coli* MG442/pVIC40, pRhtC (VKPM B-7680) has the same culture, morphological, and biochemical features as the strain VKPM B-7700 except that in addition to pRhtC, it contains a multicopy hybrid plasmid pVIC40 which ensures resistance to streptomycin (100 mg/l) and carries the genes of the threonine operon.

The *E. coli* NZ10/pRhtB, pRhtC (VKPM B-7681) strain has the same culture, morphological, and biochemical features as the strain VKPM B-7700 except that L-threonine (0.1-5 mg/ml) is used as a growth factor instead of L-isoleucine. Furthermore, it contains a multicopy hybrid plasmid pRhtB which ensures resistance to kanamycin (50 mg/ml) and carries the rhtB gene which confers resistance to homoserine (10 mg/ml) The *E. coli* NZ10/pRhtBC, (VKPM B-7682) strain has the same culture, morphological, and biochemical features as the strain VKPM B-7681 except that it contains a multicopy hybrid plasmid pRhtBC which ensures resistance to ampicillin (100 mg/l) and carries both the rhtB and rhtC genes which confer resistance to L-homoserine (10 mg/ml) and L-threonine (50 mg/ml).

<3> Method for Producing an Amino Acid

An amino acid can be efficiently produced by cultivating the bacterium in which the Rt activity, or both the Rt and Rh activity, is enhanced by amplifying a copy number of the rhtC gene, or both the rhtC and rhtB gene, as described above, and which has an ability to produce the amino acid in a culture medium, producing and causing accumulation of the amino acid in the medium, and recovering the amino acid from the medium. The amino acid is exemplified preferably by L-homoserine, L-threonine, and branched chain amino acids. The branched chain amino acids may be exemplified by L-valine, L-leucine, and L-isoleucine, and preferably exemplified by L-valine, L-leucine.

In the method of present invention, the cultivation of the bacterium belonging to the genus *Escherichia*, and the collection and purification of amino acids from the liquid medium may be performed in a manner similar to conventional methods for producing an amino acid by fermentation using a bacterium. A medium used in cultivation may be either a synthetic or a natural medium, so long as the medium includes a carbon and a nitrogen source and minerals and, if necessary, nutrients which the chosen bacterium requires for growth in appropriate amount. The carbon source may include various carbohydrates such as glucose and sucrose, and various organic acids. Depending on the assimilatory ability of the chosen bacterium, alcohol including ethanol and glycerol may be used. As the nitrogen source, ammonia, various ammonium salts as ammonium sulfate, other nitrogen compounds such as amines, a natural nitrogen source such as peptone, soybean hydrolyzate and digested fermentative microbe can be used. As minerals, monopotassium phosphate, magnesium sulfate, sodium chloride, ferrous sulfate, manganese sulfate, calcium carbonate can be used.

The cultivation is preferably under aerobic conditions, such as a shaking with aeration, and stirring. The temperature of the culture is usually 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, an 1 to 3-day cultivation leads to the accumulation of the target amino acid in the medium.

Recovering the amino acid can be performed by removing solids such as cells from the medium by centrifugation or membrane filtration after cultivation, and then collecting and purifying the target amino acid by ion exchange, concentration and crystalline fraction methods and the like.

The present invention will be more concretely explained below with reference to the following non-limiting Examples. In the Examples, an amino acid is of L-configuration unless otherwise noted.

Example 1

Obtaining of the rhtB and rhtC DNA Fragments

Step 1. Cloning of the Genes Involved in Resistance to Homoserine and Threonine into Mini-Mu Phagemid The genes involved in resistance to homoserine and threonine were cloned in vivo using mini-Mu d5005 phagemid (Groisman, E. A., et al., J. Bacteriol., 168, 357-364 (1986)). MuCts62 lysogen of the strain MG442 (Guayatiner et al., Genetika (in Russian), 14, 947-956 (1978)) was used as a donor. Freshly prepared lysate was used to infect a Mucts lysogenic derivative of strain VKPM B-513 (Hfr K10 metB). The cells were plated on M9 glucose minimal medium with methionine (50 μg/ml), kanamycin (40 μg/ml), and homoserine (10 μg/ml). Colonies which appeared after 48 hr were picked and isolated. Plasmid DNA was isolated and used to transform the strain VKPM B-513 by standard techniques. Transformants were selected on L-broth agar plates with kanamycin as above. Plasmid DNA was isolated from those which were resistance to homoserine, and the structure of the inserted fragments was analyzed by restriction mapping. It appeared that two types of inserts from different chromosome regions had been cloned from the donor. Thus, at least two different genes exist in *E. coli* that, when in multicopy, impart resistance to homoserine. One of the inserts is the rhtA gene which has already reported (ABSTRACT of 17th International Congress of Biochemistry and Molecular Biology in conjugation with 1997 Annual Meeting at the American Society for Biochemistry and Molecular Biology, San Francisco, Calif. Aug. 24-29, 1997). The other of the two inserts, a MluI-MluI fragment of 0.8 kb, imparts only the resistance to homoserine (FIG. 1).

Step 2: Identification of rhtB and rhtC Gene

The insert fragment was sequenced by the dideoxy chain termination method of Sanger. Both DNA strands were sequenced in their entirety and all junctions were overlapped. The sequencing showed that the insert fragment included f138 (nucleotide numbers 61543 to 61959 of GenBank accession number M87049) which was a known ORF (open reading frame) of unknown function present at 86 min of *E. coli* chromosome and about 350 bp of an upstream region thereof (downstream region in the sequence of M87049). The f138 had only 160 nucleotides in the 5'-flanking region and could not impart the resistance to homoserine. No termination codon is present upstream of the ORF f138 between 62160 and 61950 nucleotides of M87049. Furthermore, one ATG is present which follows a sequence which has been predicted to be a ribosome binding site. The larger ORF (nucleotide numbers 62160 to 61546) is designated as the rhtB gene. The deduced RhtB protein has a region which is highly hydrophobic and contains possible transmembrane segments.

As described below, the plasmid containing this gene conferred upon cells only resistance to high concentrations of homoserine. Since the initial SacII-SacII DNA fragment contained the second unidentified ORF, o128, the gene was subcloned and tested for its ability to confer resistance to homoserine and threonine. It proved that the plasmid containing o128 (ClaI-Eco47III fragment) conferred resistance to 50 mg/ml threonine (FIG. 1). The subcloned fragment was sequenced and found to contain an additional nucleotide (G) in the position between the 61213 and 61214 nucleotides of M87049. The nucleotide addition to the sequence eliminated a frame shift and enlarged the ORF into the 5'-flanking region up to the 60860 nucleotide. This new gene was designated rhtC. Both the rhtB and rhtC genes were found to be homologous to a transporter involved in lysine export of *Corynebacterium glutamicum*.

Example 2

The Effect of Amplification of the rhtB and rhtC Genes on Homoserine Production

Figure 2:
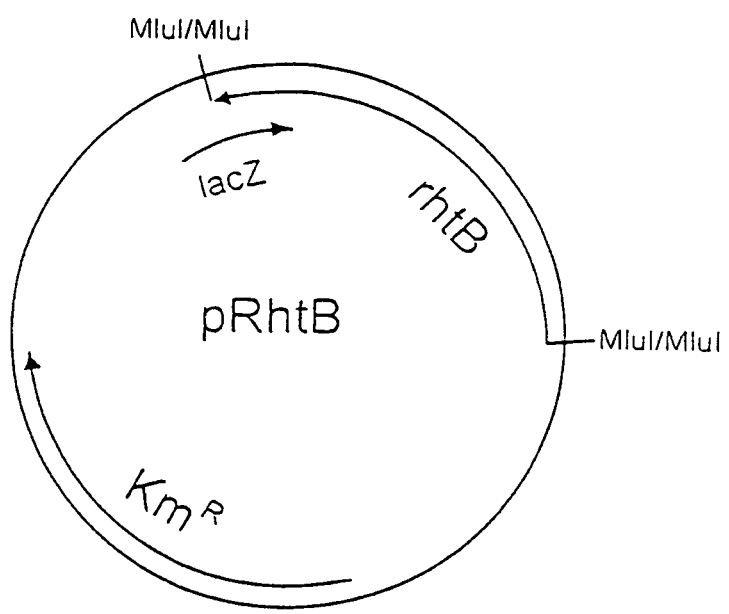
FIG. 2 shows the structure of the plasmid pRhtB which harbors the rhtB gene.

<1> Construction of the L-Homoserine-Producing Strain *E. coli* NZ10/pAL4, pRhtB, and Homoserine Production The rhtB gene was inserted into plasmid pUK21 (Vieira, J. And Messing, J., Gene, 100, 189-194 (1991)), to obtain pRhtB (FIG. 2).

Strain NZ10 of *E. coli* was transformed by plasmid pAL4 which is a pBR322 vector into which the thrA gene coding for aspartokinase-homoseine dehydrogenase I has been inserted, to obtain the strains NZ10/pAL4. The strain NZ10 is a leuB$^+$-reverted mutant thrB$^-$ obtained from the *E. coli* strain C600 (thrB, leuB) (Appleyard R. K., Genetics, 39, 440-452, 1954).

The strain NZ10/pAL4 was transformed with pUK21 or pRhtB to obtain strains NZ10/pAL4, pUK21 and NZ10/pAL4, pRhtB.

The thus obtained transformants were each cultivated at 37° C. for 18 hours in a nutrient broth with 50 mg/l kanamycin and 100 mg/l ampicillin, and 0.3 ml of the obtained culture was inoculated into 3 ml of fermentation medium having the following composition and containing 50 mg/l kanamycin and 100 mg/l ampicillin, in a 20×200 mm test tube, and cultivated at 37° C. for 48 hours with a rotary shaker. After the cultivation, an accumulated amount of homoserine in the medium and an absorbance at 560 nm of the medium were determined by known methods.

Fermentation Medium Composition (g/L):

Glucose 80

$(NH_4)_2SO_4$ 22

$K_2HPO_4$ 2

NaCl 0.8

$MgSO_4 \cdot 7H_2O$ 0.8

$FeSO_4 \cdot 7H_2O$ 0.02

$MnSO_4 \cdot 5H_2O$ 0.02

Thiamine hydrochloride 0.2

Yeast Extract 1.0

$CaCO_3$ 30

($CaCO_3$ was separately sterilized)

The results are shown in Table 1. As shown in Table 1, the strain NZ10/pAL4, pRhtB was able to cause accumulation of homoserine in a larger amount than the strain NZ10/pAL4, pUK21 in which the rhtB gene was not enhanced.

TABLE 1

| Strain | OD$_{560}$ | Accumulated amount of homoserine(g/L) |
|---|---|---|
| NZ10/pAL4, pUK21 | 14.3 | 3.3 |
| NZ10/pAL4, pRhtB | 15.6 | 6.4 |

Figure 3:
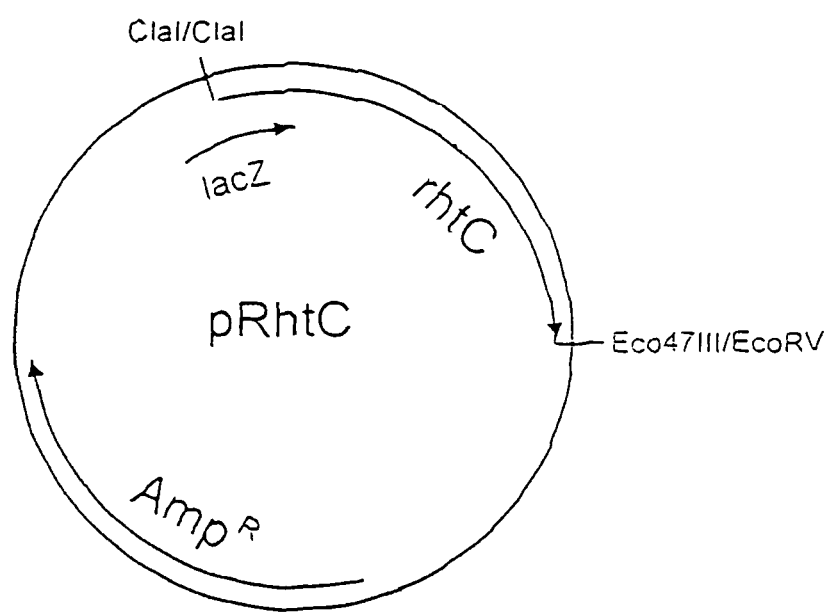
FIG. 3 shows the structure of the plasmid pRhtC which harbor the rhtC gene.

<2> Construction of the Homoserine-Producing Strain *E. coli* MG442/pRhtC and Homoserine Production The rhtC gene was inserted into pUC21 vector (Vieira, J. And Messing, J., Gene, 100, 189-194 (1991)), to obtain pRhtC (FIG. 3).

The known *E. coli* strain MG442 which can produce threonine in an amount of not less than 3 g/L (Gusyatiner, et al., 1978, Genetika (in Russian), 14:947-956) was transformed by introducing pUC21 or pRhtC to obtain the strains MG442/pUC21 and MG442/pRhtC.

The thus obtained transformants were each cultivated at 37° C. for 18 hours in a nutrient broth with 100 mg/ml ampicillin, and 0.3 ml of the obtained culture was inoculated into 3 ml of the fermentation medium described above and containing 100 mg/ml ampicillin, in a 20×200 mm test tube, and cultivated at 37° C. for 48 hours with a rotary shaker. After the cultivation, an accumulated amount of homoserine in the medium and an absorbance at 560 nm of the medium were determined by known methods. The results are shown in Table 2.

TABLE 2

| Strain | OD$_{560}$ | Accumulated amount of homoserine(g/L) |
|---|---|---|
| MG442/pUC21 | 9.7 | <0.1 |
| MG442/pRhtC | 15.2 | 9.5 |

Example 3

The Effect of Amplification of the rhtB and rhtC Genes on Threonine Production

<1> Construction of the Threonine-Producing Strain *E. coli* VG442/pVIC40, pRhtB (VKPM B-7660) and Threonine Production The strain MG442 was transformed by introducing the known plasmid pVIC40 (U.S. Pat. No. 5,175,107 (1992)) by an ordinary transformation method. Transformants were selected on LB agar plates containing 0.1 mg/ml streptomycin. Thus a novel strain MG442/pVIC40 was obtained.

The strain MG442/pVIC40 was transformed with pUK21 or pRhtB to obtain strain MG442/pVIC40, pUK21 and MG442/pVIC40, pRhtB.

The thus obtained transformants were each cultivated at 37° C. for 18 hours in a nutrient broth with 50 mg/l kanamycin and 100 mg/l streptomycin, and 0.3 ml of the obtained culture was inoculated into 3 ml of the fermentation medium described in Example 2 and containing 50 mg/l kanamycin and 100 mg/l streptomycin, in a 20×200 mm test tube, and cultivated at 37° C. for 68 hours with a rotary shaker. After the cultivation, an accumulated amount of threonine in the medium and an absorbance at 560 nm of the medium were determined by known methods.

The results are shown in Table 3. As shown in Table 3, the strain MG442/pVIC40, pRhtB was able to cause accumulation of threonine in a larger amount than the strain MG442/pVIC40, pUK21 in which the rhtB gene was not enhanced.

TABLE 3

| Strain | OD$_{560}$ | Accumulated amount of threonine (g/L) |
|---|---|---|
| MG442/pVIC40, pUK21 | 16.3 | 12.9 |
| MG442/pVIC40, pRhtB | 15.2 | 16.3 |

<2> Construction of the Threonine-Producing Strain *E. coli* VG442/pVIC40, pRhtC (VKPM B-7680) and Threonine Production The strain MG442/pVIC40 was transformed with pRhtC and pUC21. Thus the transformants MG442/pVIC40, pRhtC and MG442/pVIC40, pUC21 were obtained. In the sane manner as described above, MG442/pVIC40, pUC21 and MG442/pVIC40, pRhtC were each cultivated at 37° C. for 18 hours in a nutrient broth with 100 mg/l ampicillin and 100 mg/l streptomycin and 0.3 ml of the obtained culture was inoculated into 3 ml of the fermentation medium described above and containing 100 mg/l ampicillin and 100 mg/l streptomycin, in a 20×200 mm test tube, and cultivated at 37° C. for 46 hours with a rotary shaker. After the cultivation, an accumulated amount of threonine in the medium and an absorbance at 560 nm of the medium were determined by known methods.

The results are shown in Table 4. As shown in Table 4, the strain MG442/pVIC40, pRhtC was able to cause accumulation of threonine in a larger amount than the strain MG442/pVIC40, pUC21 in which the rhtC gene was not enhanced.

TABLE 4

| Strain | OD$_{560}$ | Accumulated amount of threonine(g/L) |
|---|---|---|
| MG442/pVIC40, pUC21 | 17.4 | 4.9 |
| MG442/pVIC40, pRhtC | 15.1 | 10.2 |

Example 4

Combined Effect of the rhtB Gene and rhtC Gene on Amino Acid Production

Figure 4:
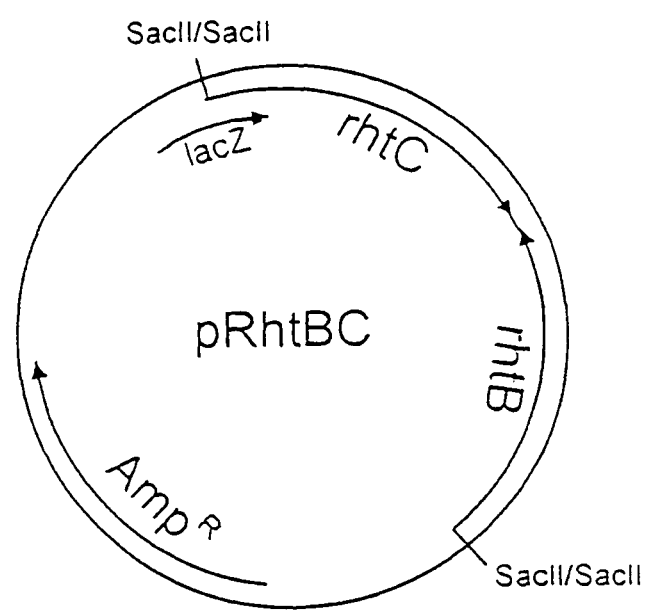
FIG. 4 shows the structure of the plasmid pRhtBC which harbors the rhtB and rhtC gene.

The SacII-SacII DNA fragment containing both the rhtB and rhtC genes was inserted into pUC21. Thus the plasmid pRhtBC was obtained which harbors the rhtB and rhtC gene (FIG. 4).

Then, the strain NZ10 was transformed with pUC21, pRhtB, pRhtC or pRhtBC, and the transformants NZ10/pUC21 (VKPM B-7685), NZ10/pRhtB (VKPM B-7683), NZ10/pRhtC (VKPM B-7684), NZ10/pRhtB, pRhtC (VKPM B-7681) and NZ10/pRhtBC (VKPM B-7682) were thus obtained.

The transformants obtained above were cultivated in the same manner as described above and the accumulated amounts of various amino acids in the medium and an absorbance at 540 nm of the medium were determined by known methods.

The results are shown in Table 5. It follows from Table 5 that there is a combined effect of the pRhtB and pRhtC on production of homoserine, valine and leucine. These results indicate that the rhtB and rhtC gene products may interact in cells.

TABLE 5

| Strain | OD$_{560}$ | Homoserine (g/L) | Valine (g/L) | Leucine (g/L) |
|---|---|---|---|---|
| NZ10/pUC21 | 18.7 | 0.6 | 0.22 | 0.16 |
| NZ10/pRhtB | 19.6 | 2.3 | 0.21 | 0.14 |
| NZ10/pRhtC | 20.1 | 0.7 | 0.2 | 0.15 |
| NZ10/pRhtBC | 21.8 | 4.2 | 0.34 | 0.44 |
| NZ10/pRhtB, pRhtC | 19.2 | 4.4 | 0.35 | 0.45 |

Example 5

Effect of the rhtB Gene and rhtC Gene on Resistance to Amino Acids

As described above, the plasmids harboring the rhtB and rhtC have a positive effect on the accumulation of some amino acids in culture broth by different strains. It proved that the pattern of accumulated amino acid was dependent on the strain genotype. The homology of the rhtB and rhtC gene products with the lysine transporter LysE of *Corynebacterium glutamicum* (Vrljic, M., Sahm, H. and Eggeling, L. (1996) *Mol. Microbiol.* 22, 815-826.) indicates the analogues function for these proteins.

Therefore, the effect of the pRhtB and pRhtC plasmids on susceptibility of the strain N99 which is a streptomycin-resistant (Str$^R$) mutant of the known strain W3350 (VKPM B-1557) to some amino acids and amino acid analogues was tested. Overnight broth cultures ($10^9$ cfu/ml) of the strains N99/pUC21, N99pUK21, N99/pRhtB and N99/pRhtC were diluted 1:100 in M9 minimal medium and grown for 5 h in the same medium. Then the log phase cultures thus obtained were diluted and about $10^4$ viable cells were applied to well-dried test plates with M9 agar (2%) containing doubling increments of amino acids or analogues. Thus the minimum inhibitory concentrations (MIC) of these compounds were examined.

The results are shown in Table 6. It follows from Table 6 that multiple copies of rhtB besides homoserine conferred increased resistance to α-amino-β-hydroxyvaleric-acid (AHVA) and S-(2-aminoethyl)-L-cysteine (AEC), and 4-aza-DL-leucine; DL-leucine; and multiple copies of rhtC gene besides threonine increased resistance to valine, histidine, and AHVA. This result indicates that of the presumed transporters, RhtB and RhtC, have specificity to several substrates (amino acids), or may show non-specific effects as a result of amplification.

TABLE 6

| | MIC (µg/ml) | | |
|---|---|---|---|
| Substrate | N99/pUC21* | N99/pRhtB | N99/pRhtC |
| L-homoserine | 1000 | 20000 | 1000 |
| L-threonine | 30000 | 40000 | 80000 |
| L-valine | 0.5 | 0.5 | 2.0 |
| L-histidine | 5000 | 5000 | 40000 |
| AHVA | 100 | 2000 | 15000 |
| AEC | 5 | 20 | 5 |
| 4-aza-DL-leucine | 50 | 100 | 50 |
| O-methyl-L-threonine | 20 | 20 | 20 |

*The same data were obtain with N99/pUK21.

What is claimed is:

1. A method of producing an L-amino acid selected from the group consisting of L-homoserine and L-threonine comprising the steps of:
   A) cultivating in a culture medium an *Escherichia coli* which has been modified to increase expression of a DNA, wherein expression of said DNA is increased by increasing the copy number of said DNA or replacing a promoter sequence of said DNA with a promoter sequence which functions in said *Escherichia coli*, wherein said DNA comprises the nucleotide sequence of nucleotides 187 to 804 of SEQ ID NO: 3;
   B) removing solids including cells from the medium; and
   C) purifying said L-amino acid from the medium obtained in step B).

2. A method of producing a branched chain L-amino acid comprising the steps of:
   A) cultivating in a culture medium an *Escherichia coli* which has been modified to increase expression of a first DNA comprising the nucleotide sequence of nucleotides 187 to 804 of SEQ ID NO: 3,
   and a second DNA comprising the nucleotide sequence of nucleotides 557 to 1171 of SEQ ID NO: 1,
   wherein said expression is increased by increasing the copy number of said first and second DNAs or replacing a promoter sequence of said first and second DNAs with a promoter sequence which functions in said *Escherichia coli*;
   B) removing solids including cells from the medium, and
   C) purifying said branched chain L-amino acid from the medium obtained in step B).

3. The method according to claim 2, wherein said branched chain L-amino acid is L-valine or L-leucine.

4. A method of producing an L-amino acid selected from the group consisting of L-homoserine and L-threonine comprising the steps of:
   A) cultivating in a culture medium an *Escherichia coli* which has been modified to increase expression of a DNA, wherein expression of said DNA is increased by increasing the copy number of said DNA or replacing a promoter sequence of said DNA with a promoter sequence which functions in said *Escherichia coli*, wherein said DNA comprises a nucleotide sequence that encodes a protein comprising the amino acid sequence of SEQ ID NO:4;
   B) removing solids including cells from the medium; and
   C) purifying said L-amino acid from the medium obtained in step B).

5. A method of producing a branched chain L-amino acid comprising the steps of:
   A) cultivating in a culture medium an *Escherichia coli* which has been modified to increase expression of a first DNA that comprises a nucleotide sequence encoding a protein comprising the amino acid sequence of SEQ ID NO: 4,
   and a second DNA that comprises a nucleotide sequence encoding a protein comprising the amino acid sequence of SEQ ID NO: 2,
   wherein said expression is increased by increasing the copy number of said first and second DNAs or replacing a promoter sequence of said first and second DNAs with a promoter sequence which functions in said *Escherichia coli*;

B) removing solids including cells from the medium, and
C) purifying said branched chain L-amino acid from the medium obtained in step B).

6. The method according to claim 5, wherein said branched chain L-amino acid is L-valine or L-leucine.

* * * * *

SEQUENCE LISTING

<160> NUMBER OF SEQ ID NOS: 4

<210> SEQ ID NO 1
<211> LENGTH: 1231
<212> TYPE: DNA
<213> ORGANISM: Escherichia coli
<220> FEATURE:
<221> NAME/KEY: CDS
<222> LOCATION: (557)..(1171)

<400> SEQUENCE: 1

```
agaaataatg tggagatcgc accgcccatc gaatgtgcca gtatatagcg tttacgccac      60
ggaccgggct gaacctcctg ctgccagaat gccgccagat catcaacata atcattaaag     120
cgattaacat gcccgagatg cggatcggct aacaggcgac cggaacgtcc ctgcccgcga     180
tggtcgatga ttaagacatc aaaccccaaa tggaacaggt cataggccag ttccgcatat     240
tttacgtagc tctcaatacg ccccgggcag atgactacca cccggtcatg gtgctgtgcg     300
cgaaaacgga caaagcgcac cggaatgtca tccacaccag taaactctgc ttcatcacgc     360
tgacgccaga aatcagtcag cggtcccatg gtaaaagcag caaacgcgtt ttctcttgtt     420
tcccagtctt tttgctgctg aaacatcggg taatctgcct cttaaaccac gtaaaatcgt     480 ttttttttagc gtgcctgaca caacgctgcg acagtagcgt attgtggcac aaaaatagac     540
acaccgggag ttcatc atg acc tta gaa tgg tgg ttt gcc tac ctg ctg aca      592
                   Met Thr Leu Glu Trp Trp Phe Ala Tyr Leu Leu Thr
                    1               5                   10 tcg atc att tta acg ctg tcg cca ggc tct ggt gca atc aac act atg        640
Ser Ile Ile Leu Thr Leu Ser Pro Gly Ser Gly Ala Ile Asn Thr Met
         15                  20                  25 acc acc tcg ctc aac cac ggt tat ccg gcc ggt ggc gtc tat tgc tgg        688
Thr Thr Ser Leu Asn His Gly Tyr Pro Ala Gly Gly Val Tyr Cys Trp
     30                  35                  40 gct tca gac cgg act ggc gat tca tat tgt gct ggt tgg cgt ggg gtt        736
Ala Ser Asp Arg Thr Gly Asp Ser Tyr Cys Ala Gly Trp Arg Gly Val
45                  50                  55                  60 ggg acg cta ttt tcc cgc tca gtg att gcg ttt gaa gtg ttg aag tgg        784
Gly Thr Leu Phe Ser Arg Ser Val Ile Ala Phe Glu Val Leu Lys Trp
                 65                  70                  75 gca ggc gcg gct tac ttg att tgg ctg gga atc cag cag tgg cgc gcc        832
Ala Gly Ala Ala Tyr Leu Ile Trp Leu Gly Ile Gln Gln Trp Arg Ala
             80                  85                  90 gct ggt gca att gac ctt aaa tcg ctg gcc tct act caa tcg cgt cga        880
Ala Gly Ala Ile Asp Leu Lys Ser Leu Ala Ser Thr Gln Ser Arg Arg
```

```
                    95                  100                 105
cat ttg ttc cag cgc gca gtt ttt gtg aat ctc acc aat ccc aaa agt        928
His Leu Phe Gln Arg Ala Val Phe Val Asn Leu Thr Asn Pro Lys Ser
    110                 115                 120 att gtg ttt ctg gcg gcg cta ttt ccg caa ttc atc atg ccg caa cag        976
Ile Val Phe Leu Ala Ala Leu Phe Pro Gln Phe Ile Met Pro Gln Gln
125                 130                 135                 140 ccg caa ctg atg cag tat atc gtg ctc ggc gtc acc act att gtg gtc       1024
Pro Gln Leu Met Gln Tyr Ile Val Leu Gly Val Thr Thr Ile Val Val
                145                 150                 155 gat att att gtg atg atc ggt tac gcc acc ctt gct caa cgg att gct       1072
Asp Ile Ile Val Met Ile Gly Tyr Ala Thr Leu Ala Gln Arg Ile Ala
                    160                 165                 170 cta tgg att aaa gga cca aag cag atg aag gcg ctg aat aag att ttc       1120
Leu Trp Ile Lys Gly Pro Lys Gln Met Lys Ala Leu Asn Lys Ile Phe
                175                 180                 185 ggc tcg ttg ttt atg ctg gtg gga gcg ctg tta gca tcg gcg agg cat       1168
Gly Ser Leu Phe Met Leu Val Gly Ala Leu Leu Ala Ser Ala Arg His
        190                 195                 200 gcg tgaaaaataa tgtcggatgc ggcgtaaacg ccttatccga cttactctga            1221
Ala
205 agacgcgtct                                                            1231

<210> SEQ ID NO 2
<211> LENGTH: 205
<212> TYPE: PRT
<213> ORGANISM: Escherichia coli

<400> SEQUENCE: 2

Met Thr Leu Glu Trp Trp Phe Ala Tyr Leu Leu Thr Ser Ile Ile Leu
1               5                   10                  15

Thr Leu Ser Pro Gly Ser Gly Ala Ile Asn Thr Met Thr Thr Ser Leu
            20                  25                  30

Asn His Gly Tyr Pro Ala Gly Gly Val Tyr Cys Trp Ala Ser Asp Arg
        35                  40                  45

Thr Gly Asp Ser Tyr Cys Ala Gly Trp Arg Gly Val Gly Thr Leu Phe
    50                  55                  60

Ser Arg Ser Val Ile Ala Phe Glu Val Leu Lys Trp Ala Gly Ala Ala
65                  70                  75                  80

Tyr Leu Ile Trp Leu Gly Ile Gln Gln Trp Arg Ala Ala Gly Ala Ile
                85                  90                  95

Asp Leu Lys Ser Leu Ala Ser Thr Gln Ser Arg Arg His Leu Phe Gln
            100                 105                 110

Arg Ala Val Phe Val Asn Leu Thr Asn Pro Lys Ser Ile Val Phe Leu
        115                 120                 125

Ala Ala Leu Phe Pro Gln Phe Ile Met Pro Gln Gln Pro Gln Leu Met
    130                 135                 140

Gln Tyr Ile Val Leu Gly Val Thr Thr Ile Val Val Asp Ile Ile Val
145                 150                 155                 160

Met Ile Gly Tyr Ala Thr Leu Ala Gln Arg Ile Ala Leu Trp Ile Lys
                165                 170                 175

Gly Pro Lys Gln Met Lys Ala Leu Asn Lys Ile Phe Gly Ser Leu Phe
            180                 185                 190

Met Leu Val Gly Ala Leu Leu Ala Ser Ala Arg His Ala
        195                 200                 205
```

<210> SEQ ID NO 3
<211> LENGTH: 840
<212> TYPE: DNA
<213> ORGANISM: Escherichia coli
<220> FEATURE:
<221> NAME/KEY: CDS
<222> LOCATION: (187)..(804)

<400> SEQUENCE: 3

```
atgccgatca ccgccagcga aatgctcagc gttaacggcg ttgggatgcg caagctggaa      60
cgctttggca aaccgtttat ggcgctgatt cgtgcgcatg ttgatggcga tgacgaagag     120
tagtcagcag cataaaaaag tgccagtatg aagactccgt aaacgtttcc ccgcgagtc      180 aaatgt atg ttg atg tta ttt ctc acc gtc gcc atg gtg cac att gtg        228
       Met Leu Met Leu Phe Leu Thr Val Ala Met Val His Ile Val
       1               5                   10 gcg ctt atg agc ccc ggt ccc gat ttc ttt ttt gtc tct cag acc gct        276
Ala Leu Met Ser Pro Gly Pro Asp Phe Phe Phe Val Ser Gln Thr Ala
15                  20                  25                  30 gtc agt cgt tcc cgt aaa gaa gcg atg atg ggc gtg ctg ggc att acc        324
Val Ser Arg Ser Arg Lys Glu Ala Met Met Gly Val Leu Gly Ile Thr
                35                  40                  45 tgc ggc gta atg gtt tgg gct ggg att gcg ctg ctt ggc ctg cat ttg        372
Cys Gly Val Met Val Trp Ala Gly Ile Ala Leu Leu Gly Leu His Leu
            50                  55                  60 att atc gaa aaa atg gcc tgg ctg cat acg ctg att atg gtg ggc ggt        420
Ile Ile Glu Lys Met Ala Trp Leu His Thr Leu Ile Met Val Gly Gly
65                  70                  75 ggc ctg tat ctc tgc tgg atg ggt tac cag atg cta cgt ggt gca ctg        468
Gly Leu Tyr Leu Cys Trp Met Gly Tyr Gln Met Leu Arg Gly Ala Leu
        80                  85                  90 aaa aaa gag gcg gtt tct gca cct gcg cca cag gtc gag ctg gcg aaa        516
Lys Lys Glu Ala Val Ser Ala Pro Ala Pro Gln Val Glu Leu Ala Lys
95                  100                 105                 110 agt ggg cgc agt ttc ctg aaa ggt tta ctg acc aat ctc gct aat ccg        564
Ser Gly Arg Ser Phe Leu Lys Gly Leu Leu Thr Asn Leu Ala Asn Pro
                115                 120                 125 aaa gcg att atc tac ttt ggc tcg gtg ttc tca ttg ttt gtc ggt gat        612
Lys Ala Ile Ile Tyr Phe Gly Ser Val Phe Ser Leu Phe Val Gly Asp
            130                 135                 140 aac gtt ggc act acc gcg cgc tgg ggc att ttt gcg ctg atc att gtc        660
Asn Val Gly Thr Thr Ala Arg Trp Gly Ile Phe Ala Leu Ile Ile Val
145                 150                 155 gaa acg ctg gcg tgg ttt acc gtc gtt gcc agc ctg ttt gcc ctg ccg        708
Glu Thr Leu Ala Trp Phe Thr Val Val Ala Ser Leu Phe Ala Leu Pro
        160                 165                 170 caa atg cgc cgt ggt tat caa cgt ctg gcg aag tgg att gat ggt ttt        756
Gln Met Arg Arg Gly Tyr Gln Arg Leu Ala Lys Trp Ile Asp Gly Phe
175                 180                 185                 190 gcc ggg gcg tta ttt gcc gga ttt ggc att cat ttg att att tcg cgg        804
Ala Gly Ala Leu Phe Ala Gly Phe Gly Ile His Leu Ile Ile Ser Arg
                195                 200                 205 tgatgccaga cgcgtcttca gagtaagtcg gataag                                840
```

<210> SEQ ID NO 4
<211> LENGTH: 206
<212> TYPE: PRT
<213> ORGANISM: Escherichia coli

<400> SEQUENCE: 4

-continued

```
Met Leu Met Leu Phe Leu Thr Val Ala Met Val His Ile Val Ala Leu
1               5                   10                  15

Met Ser Pro Gly Pro Asp Phe Phe Phe Val Ser Gln Thr Ala Val Ser
            20                  25                  30

Arg Ser Arg Lys Glu Ala Met Met Gly Val Leu Gly Ile Thr Cys Gly
            35                  40                  45

Val Met Val Trp Ala Gly Ile Ala Leu Leu Gly Leu His Leu Ile Ile
    50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
            85                  90                  95

Glu Ala Val Ser Ala Pro Ala Pro Gln Val Glu Leu Ala Lys Ser Gly
            100                 105                 110

Arg Ser Phe Leu Lys Gly Leu Leu Thr Asn Leu Ala Asn Pro Lys Ala
            115                 120                 125

Ile Ile Tyr Phe Gly Ser Val Phe Ser Leu Phe Val Gly Asp Asn Val
            130                 135                 140

Gly Thr Thr Ala Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
            180                 185                 190

Ala Leu Phe Ala Gly Phe Gly Ile His Leu Ile Ile Ser Arg
            195                 200                 205
```